United States Patent
Agro et al.

[11] Patent Number: 6,007,522
[45] Date of Patent: Dec. 28, 1999

[54] SINGLE OPERATOR EXCHANGE BILIARY CATHETER

[75] Inventors: Mark Agro, Mendon; Charles Warich, Milford; Gary McAlister, Franklin; Gordon Nelson, North Attleboro; Daniel Brillo, North Brighton; Ronald Paille, Attleboro, all of Mass.

[73] Assignee: Boston Scientific Corporation, Natick, Mass.

[21] Appl. No.: 08/926,200

[22] Filed: Sep. 9, 1997

Related U.S. Application Data

[60] Provisional application No. 60/025,235, Sep. 13, 1996.

[51] Int. Cl.$^6$ .......................... A61M 5/00; A61M 25/00
[52] U.S. Cl. .......................... 604/264; 604/528; 604/533
[58] Field of Search .................. 604/93, 19, 28, 604/49, 54, 158, 164–166, 171, 96, 280–283, 160, 528, 533; 606/46; 600/433–435, 585

[56] References Cited

U.S. PATENT DOCUMENTS

| | | | |
|---|---|---|---|
| 4,696,668 | 9/1987 | Wilcox | 604/28 |
| 4,748,982 | 6/1988 | Horzewski et al. | 128/344 |
| 4,781,677 | 11/1988 | Wilcox | 604/28 |
| 4,905,667 | 3/1990 | Foerster et al. | 128/4 |
| 4,917,103 | 4/1990 | Gambale et al. | 128/772 |
| 4,927,418 | 5/1990 | Dake et al. | 604/264 |
| 4,928,693 | 5/1990 | Goodin et al. | 128/637 |
| 4,988,356 | 1/1991 | Crittenden et al. | 606/192 |
| 5,040,548 | 8/1991 | Yock | 128/898 |
| 5,061,273 | 10/1991 | Yock | 606/194 |
| 5,135,535 | 8/1992 | Kramer | 606/194 |
| 5,147,377 | 9/1992 | Sahota | 606/194 |
| 5,167,634 | 12/1992 | Corrigan, Jr. et al. | 604/160 |
| 5,195,978 | 3/1993 | Schiffer | 604/161 |
| 5,205,822 | 4/1993 | Johnson et al. | 604/96 |
| 5,232,445 | 8/1993 | Bonzel | 604/96 |
| 5,279,562 | 1/1994 | Sirhan et al. | 604/96 |
| 5,282,479 | 2/1994 | Havran | 604/171 |
| 5,290,232 | 3/1994 | Johnson et al. | 604/96 |
| 5,290,241 | 3/1994 | Kraus et al. | 604/161 |
| 5,300,085 | 4/1994 | Yock | 606/191 |
| 5,306,247 | 4/1994 | Pfenninger | 604/96 |
| 5,308,318 | 5/1994 | Plassche, Jr. | 604/54 |
| 5,324,269 | 6/1994 | Miraki | 604/160 |
| 5,334,143 | 8/1994 | Carroll | 604/54 |
| 5,334,187 | 8/1994 | Fischell et al. | 604/194 |
| 5,350,395 | 9/1994 | Yock | 606/194 |
| 5,397,302 | 3/1995 | Weaver et al. | 604/54 |
| 5,451,233 | 9/1995 | Yock | 606/194 |
| 5,496,346 | 3/1996 | Horzewski et al. | 606/154 |
| 5,501,227 | 3/1996 | Yock | 128/662.06 |
| 5,536,248 | 7/1996 | Weaver et al. | 604/54 |

(List continued on next page.)

FOREIGN PATENT DOCUMENTS 0 388 112 A2  9/1990  European Pat. Off. .

OTHER PUBLICATIONS

"Double–channel fistulotome for endoscopic drainage of pancreatic pseudocyst", *Gastrointestinal Endoscopy*, vol. 37, No. 3, May/Jun. 1991, pp. 356–357.

"Two new methods for selective bile duct cannulation and sphincterotomy", *Gastrointestinal Endoscopy*, vol. 33, No. 6, Dec. 1987, pp. 438–440.

*Primary Examiner*—Wynn Wood Coggins
*Assistant Examiner*—Sharon Finkel
*Attorney, Agent, or Firm*—Crompton,Seager & Tufte, LLC

[57] ABSTRACT

Catheter for use in biliary procedures, including a shaft having a proximal end and a distal end. A guide wire lumen is carried by the shaft extending from a location proximal the distal end of the shaft to a location proximate the distal end of the shaft. A channel extending longitudinally between a first end and a second end is included for accessing the guide wire lumen from a location exterior the catheter shaft located distal the proximal end of the shaft. The catheter may be used in rapid exchange catheter procedures. The channel may be U-shaped, containing the guide wire yet allowing radial removal of the guide wire from the channel. The catheter may also be part of a device including an endoscope exchange sheath for constraining guide wire movement to the catheter channel while inside a large endoscope working channel.

41 Claims, 13 Drawing Sheets

U.S. PATENT DOCUMENTS

| | | | |
|---|---|---|---|
| 5,540,236 | 7/1996 | Ginn | 128/772 |
| 5,599,299 | 2/1997 | Weaver et al. | 604/54 |
| 5,599,300 | 2/1997 | Weaver et al. | 604/54 |
| 5,626,600 | 5/1997 | Horzewski et al. | 606/194 |
| 5,706,827 | 1/1998 | Ehr et al. | 604/96 |
| 5,788,681 | 8/1998 | Weaver et al. | 604/280 |
| 5,843,028 | 12/1998 | Weaver et al. | 604/96 |
| 5,849,016 | 12/1998 | Suhr | 606/108 |
| B1 4,762,129 | 7/1991 | Bonzel | 606/194 |

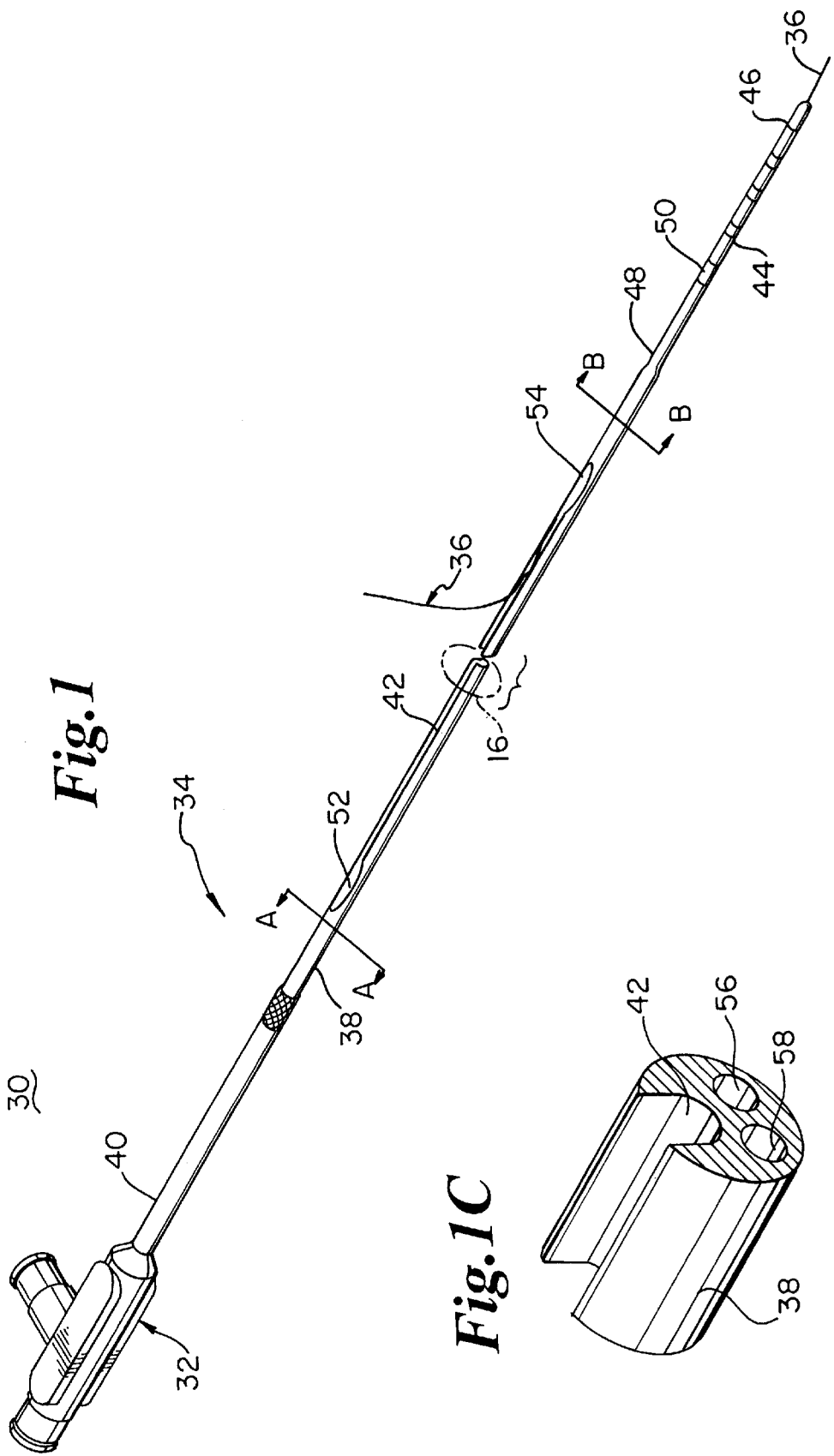

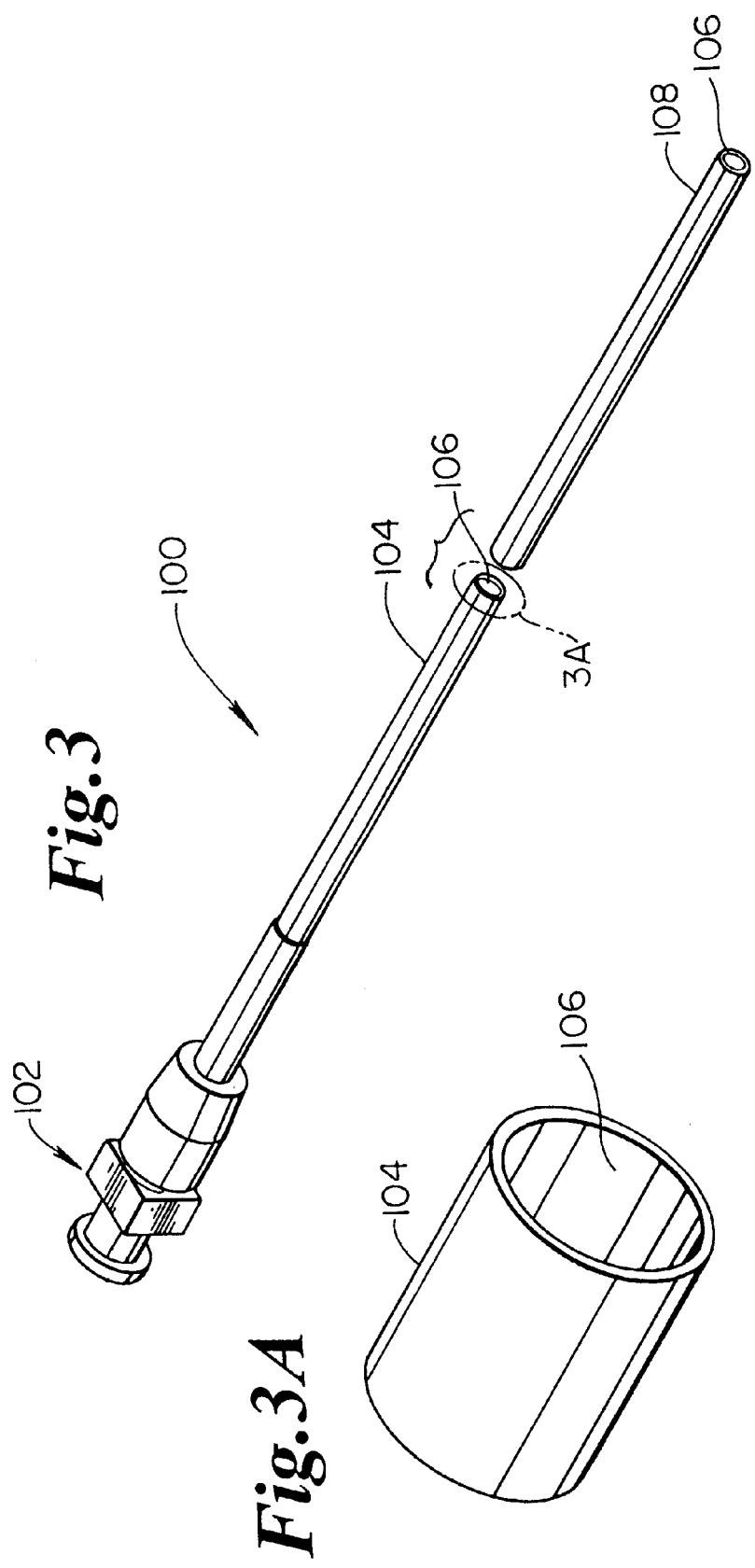

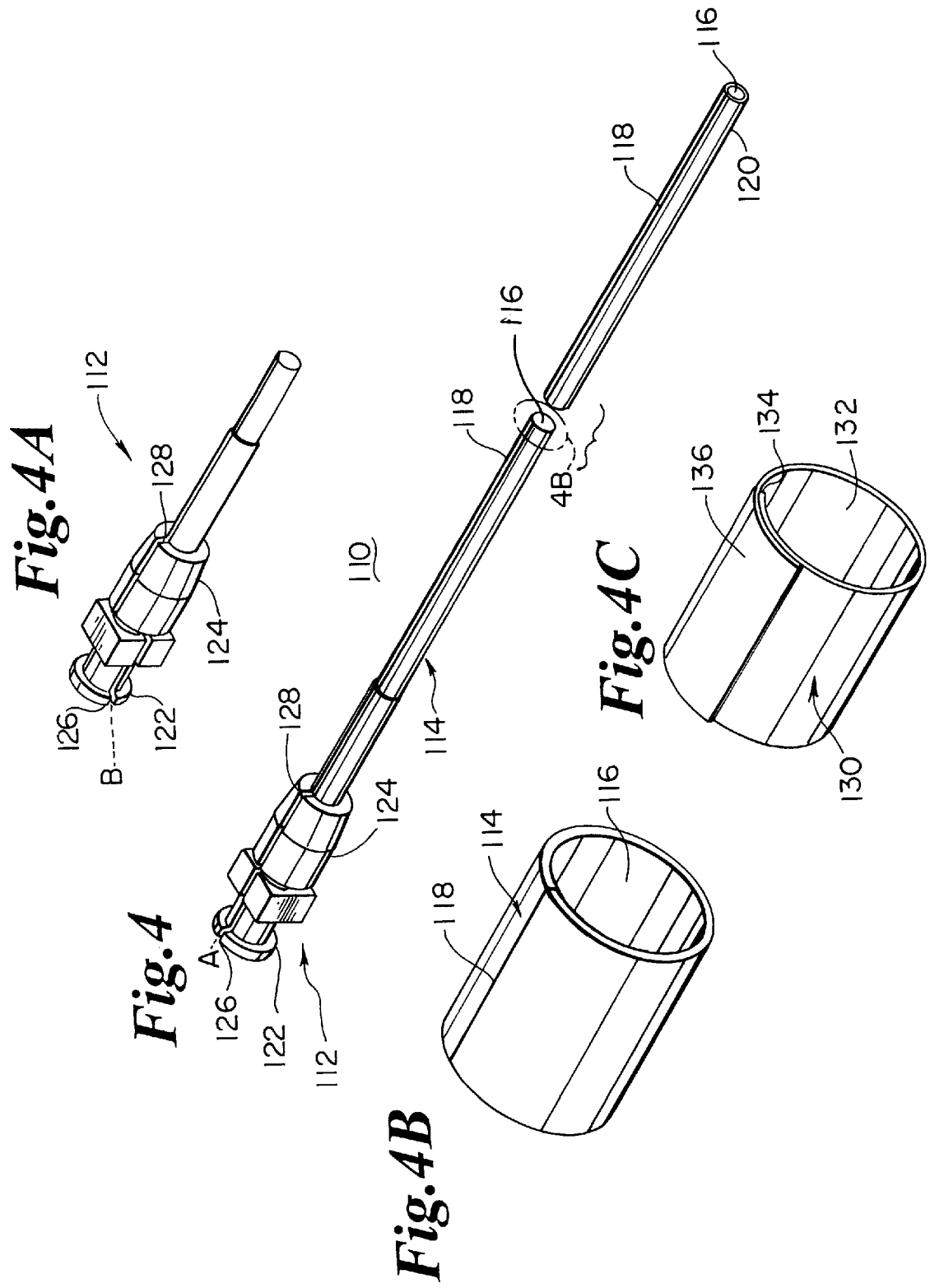

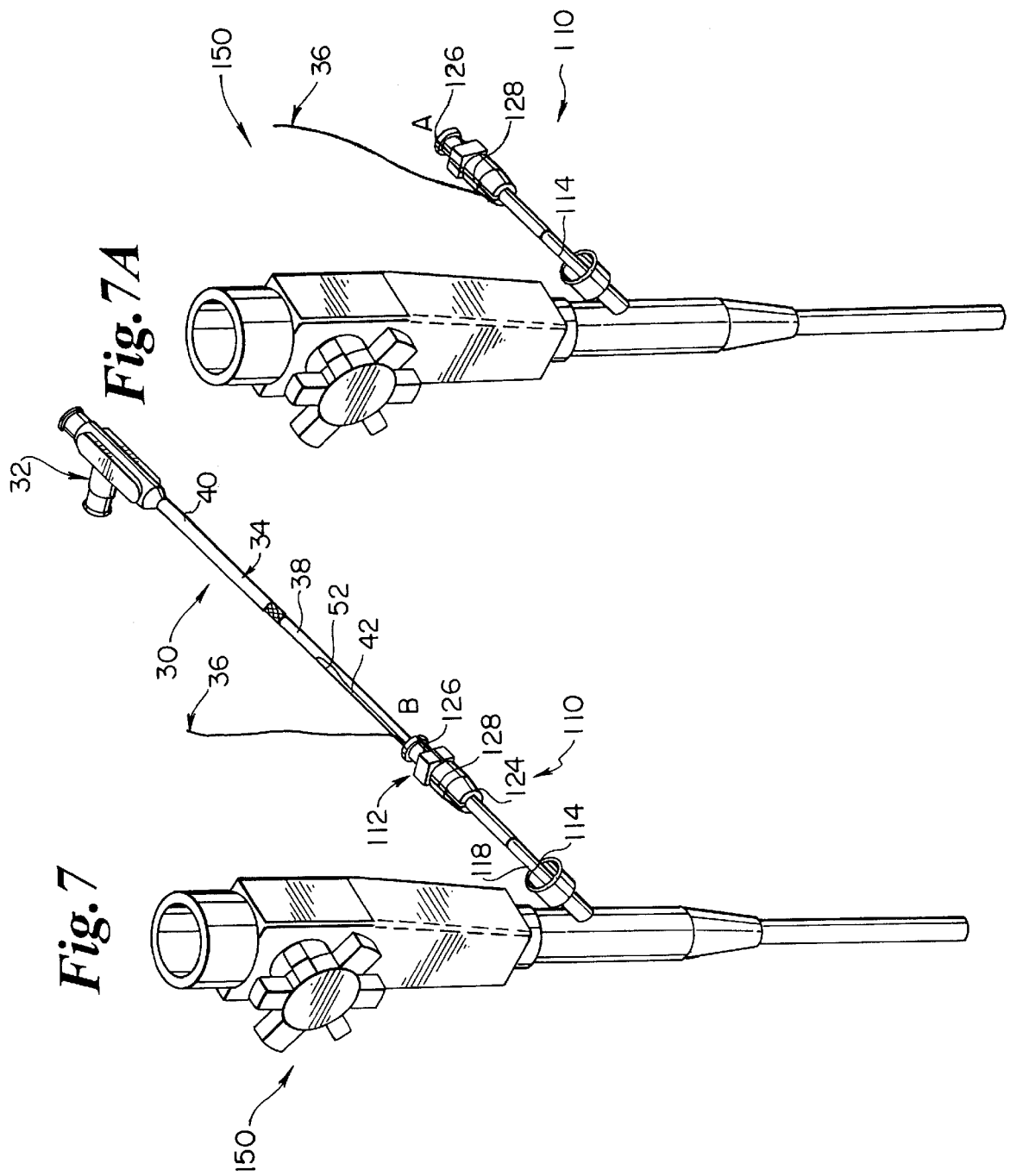

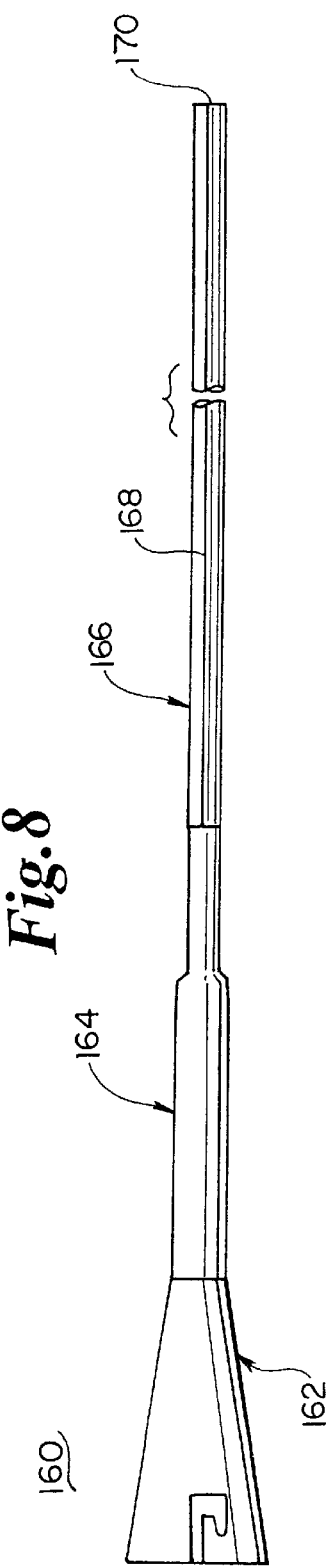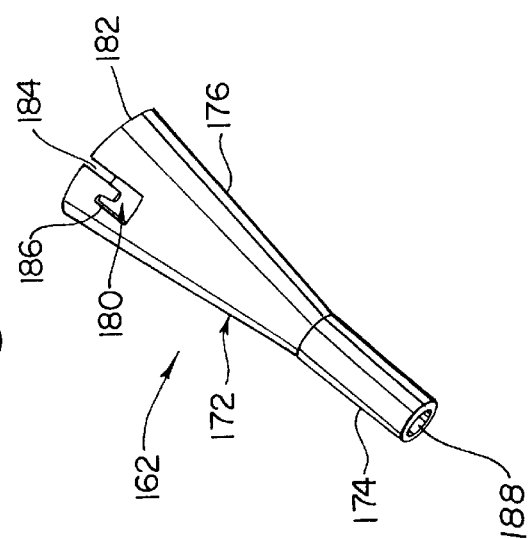

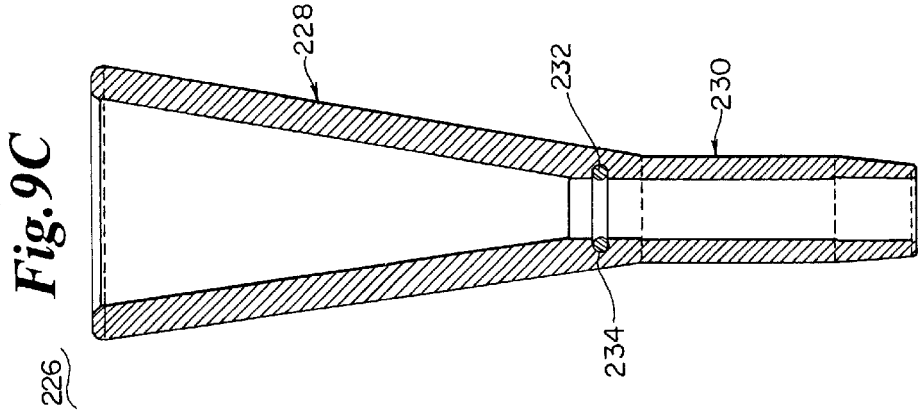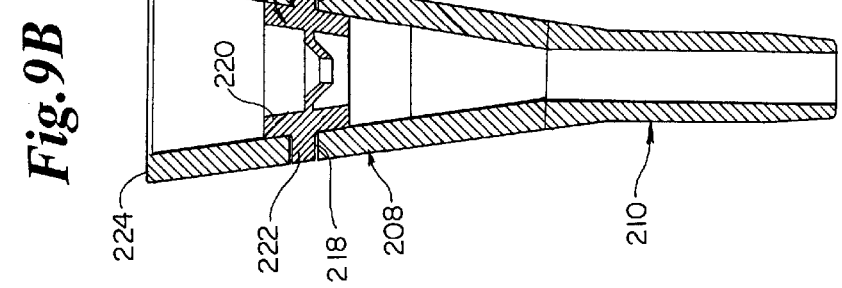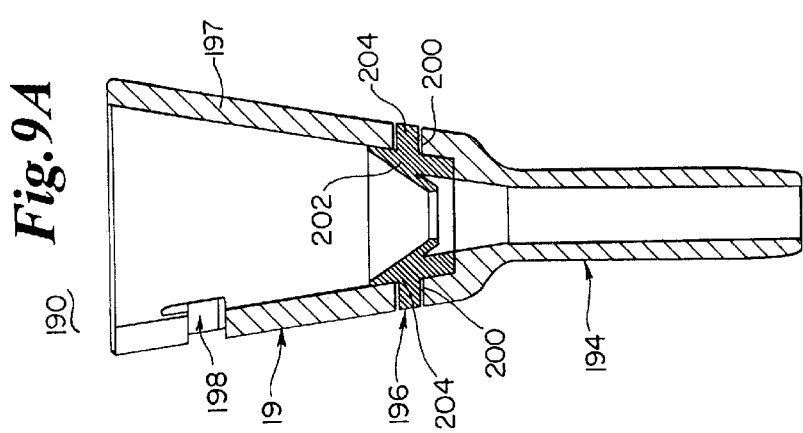

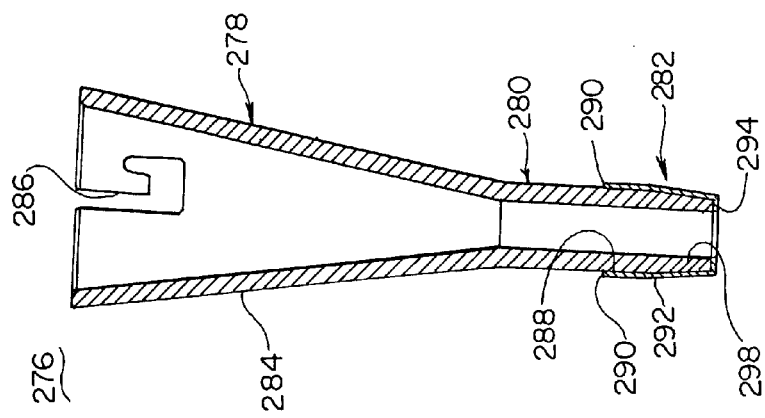
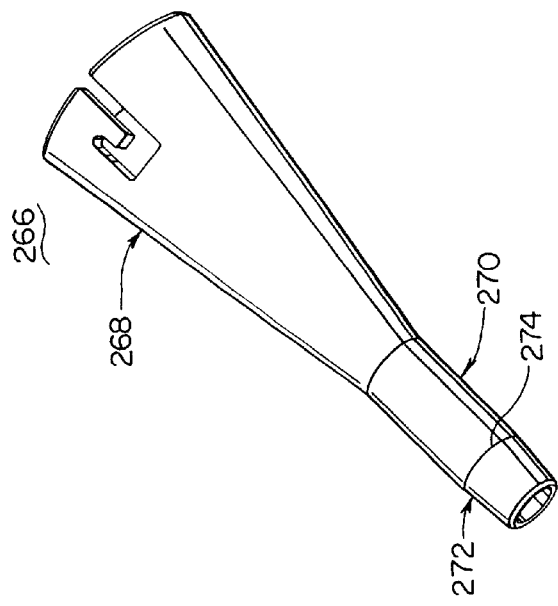
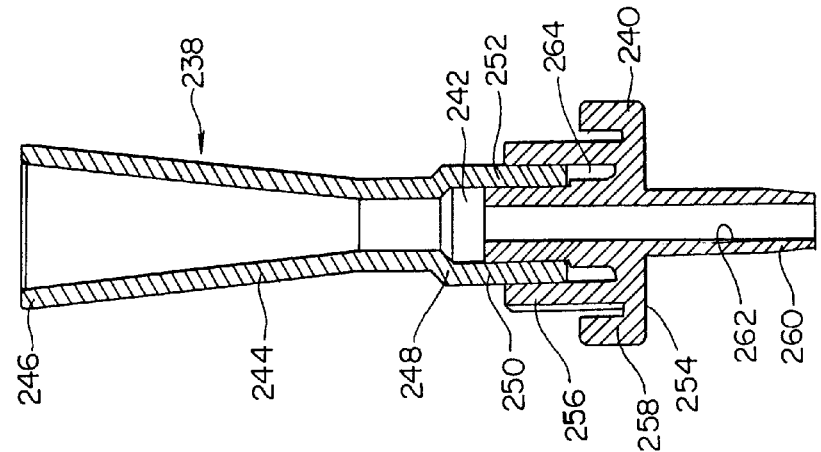

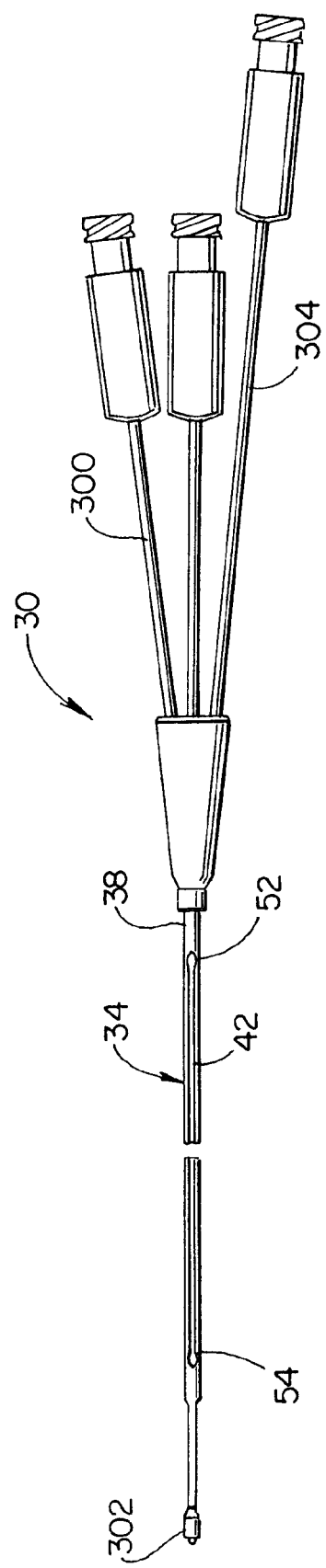

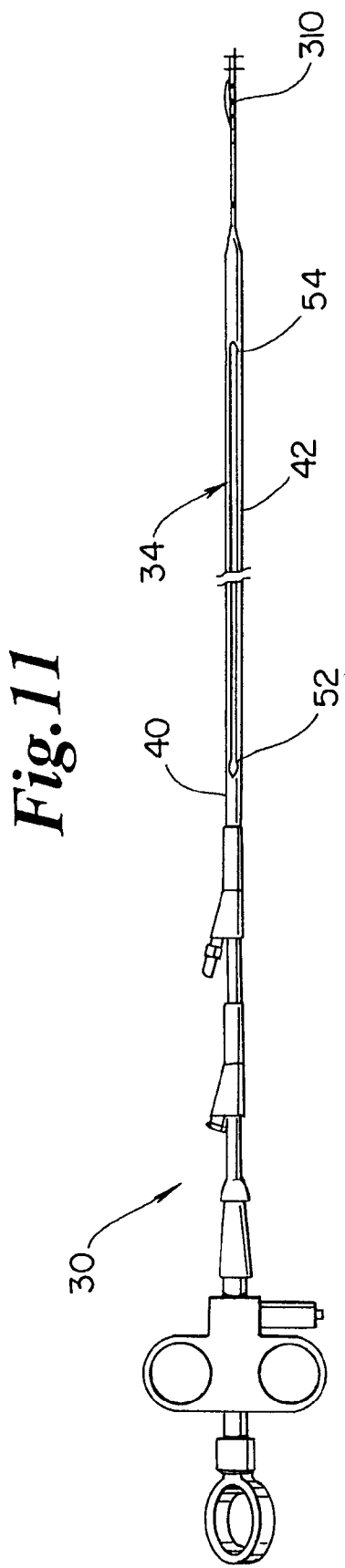

SINGLE OPERATOR EXCHANGE BILIARY CATHETER

This application claims priority under 35 U.S.C. §119(e) to provisional application U.S. Serial No. 60/025,235, filed Sep. 13, 1996, entitled "Single Operator Exchange Biliary Catheter".

FIELD OF THE INVENTION

The present invention relates to a catheter for use in catheter procedures accessed through the alimentary canal within the human anatomy and methods of using such a catheter. The catheter is particularly useful in conjunction with an endoscope for accessing the biliary tree. The present invention includes a catheter having a single operator exchange or rapid exchange feature which permits the use of a shorter guide wire, allows less time consuming procedures, and allows for larger diameter ancillary lumens within the catheter.

DESCRIPTION OF THE PRIOR ART

Endoscopic procedures for treating abnormal pathologies within the alimentary canal system and biliary tree (including the biliary, hepatic, and pancreatic ducts) are increasing in number. The endoscope provides access to the general area of a desired duct using direct visualization. However, the duct itself must be navigated using a catheter in conjunction with fluoroscopy and guide wires.

Catheters are known for treatment of targeted anatomical regions. Known methods and devices for using biliary catheters for accessing the biliary tree for performing catheter procedures are disclosed in Weaver et al., U.S. Pat. No. 5,397,302 and Karpiel, U.S. Pat. No. 5,320,602, the disclosures of which are herein incorporated by reference.

In general, for treatment of an abnormal pathology within a patient's biliary tree, an endoscope is first introduced into the mouth of the patient. The endoscope includes a proximal end and a distal end, and has a lumen extending longitudinally between the proximal and distal ends. The endoscope is guided through the patient's alimentary tract or canal until an opening at the distal end of the endoscope is proximate the area to receive treatment. At this point, the endoscope allows other components, such as a catheter, to access the targeted area.

For visualization or treatment within the biliary tree, the distal end of the endoscope is positioned proximate the papilla of vater leading to the common bile duct and the pancreatic duct. A catheter is guided through the lumen of the endoscope until a distal tip of the catheter emerges from the opening at the distal end of the endoscope.

The catheter may be used for accessing the biliary tree. The distal end of the catheter is guided through the orifice to the papilla of vater (located between the sphincter of oddi) leading to the common bile duct and the pancreatic duct. A guide wire may be used in conjunction with the catheter to facilitate accessing a desired location within the biliary tree. The guide wire is inserted in an opening at a proximal end of the catheter and guided through the catheter until it emerges from the distal end of the catheter.

If visualization of the common bile duct is desired, the guide wire is guided into the common bile duct. The catheter is advanced over the guide wire, as previously described, until the distal end of the catheter is positioned in the common bile duct at the desired location. The catheter is now in position for delivery of contrast media for fluoroscopic visualization of anatomical detail within the common bile duct. Once the guide wire is in place relative to the targeted area, it is highly desirable to maintain that position of the guide wire during subsequent catheter procedures, including catheter exchange procedures.

Present biliary endoscopic procedures include the use of multi-lumen catheters for endoscopic retrograde cholangiopancreatography, endoscopic retrograde sphincterotomy, the use of balloon catheters having retrieval balloons, and other therapeutic and diagnostic procedures. As described in general above, these present biliary endoscopic procedures are performed using guide wire techniques. The present devices utilized in these procedures are at least 180 cm long since they pass through the endoscope, which is commonly at least 150 cm long. Therefore, when using a standard catheter having a guide wire lumen extending the full length of the catheter, guide wires used during these procedures must be at least 400 cm in length to accommodate the exchanging of different devices while maintaining access and position within the biliary tree. The exchange of devices over a 400 cm guide wire is both time consuming and cumbersome.

Due to the length of the guide wire, physicians require at least two assistants in the room to perform the biliary endoscopic procedure. Typically, one assistant is responsible for the patient and device-related concerns, while the other assistant is responsible for the guide wire. The additional hands required due to the length of the guide wire results in a relatively more time consuming and costly procedure.

It is desirable to have an exchange catheter suitable for use within the alimentary canal for accessing targeted anatomical regions, such as the biliary tree, having features which facilitate rapid exchange and allow an exchange procedure to be performed by a single operator. It is desirable to have a biliary exchange catheter which may be used in connection with a shorter guide wire, and requires less personnel for performing biliary procedures. It is desirable to have a biliary exchange catheter which limits the amount of guide wire over which the catheter must travel.

It is also desirable to have a biliary rapid exchange catheter which may be convertible for use between conventional guide wire techniques and rapid exchange guide wire techniques. It is desirable to have a biliary rapid exchange catheter which is easily removable from the guide wire, and adaptable for use with most catheter systems used within the alimentary canal.

SUMMARY OF THE INVENTION

The present invention relates to a biliary catheter for use in biliary endoscopic procedures which incorporates rapid exchange catheter features. Rapid exchange features include an effective guide wire lumen which is much shorter than the overall catheter length to facilitate rapid exchange of the device over the guide wire.

In one preferred embodiment, the present invention is an improved catheter for use in biliary procedures which includes a shaft having a proximal end and a distal end. The improvement includes a guide wire lumen carried by the shaft extending from a location proximal of the distal end of the shaft to a location proximate the distal end of the shaft. Means are provided for accessing the guide wire lumen from a location exterior to the catheter shaft, located a substantial distance distal of the proximal end of the shaft.

The guide wire lumen may be formed integral with the shaft. The means for accessing the guide wire lumen may include an open channel extending through a wall of the catheter shaft.

More particularly, the preferred means or channel for accessing the guide wire lumen includes a channel distal end through the wall of the catheter shaft into the guide wire lumen located proximal of the distal end of the shaft and a channel proximal end into the guide wire lumen located proximal of the intermediate opening. The channel is further defined by a longitudinal opening to the exterior of the catheter shaft extending between the channel distal end and the channel proximal end in communication with the guide wire lumen. The longitudinal opening preferably is equal to or greater than the diameter of a guide wire used therewith.

In one embodiment, the open channel has a "U" shape. The open channel is in communication with the guide wire lumen, allowing the guide wire to run within the guide wire lumen and U-channel over the length of the catheter.

Additionally, the preferred embodiment includes an endoscope sheath selectively positioned about at least a portion of the channel so as to provide an inside diameter sufficiently small to constrain the guide wire substantially within the channel. The endoscope sheath may be used in conjunction with an endoscope working channel large enough to otherwise allow the guide wire to move radially out of the open channel and become pinched between the catheter exterior and the endoscope working channel wall interior. The sheath allows the guide wire to be externally radially accessible, yet not loose within the endoscope working channel, with the sheathed catheter and guide wire presenting a generally circular profile to the endoscope working channel.

In the preferred embodiment, the endoscope sheath includes a longitudinal slit, allowing for selective guide wire radial removal through the slit. This configuration facilitates expedient sheath removal and exchange, while maintaining guide wire and/or catheter position within the patient. In yet another embodiment, the endoscope sheath has a circumferential overlap along its length, providing an alternate opening for radially removing a guide wire.

In another embodiment, the present invention includes a method of positioning a biliary catheter including a shaft having a proximal end and a distal end, within a patient's alimentary canal. The method includes the step of providing a catheter with a guide wire lumen therein. The guide wire lumen extends from a location proximal of the distal end of the shaft to a location proximate the distal end of the shaft. An open channel is provided through a sidewall of the shaft into the guide wire lumen. The channel is located distal of the proximal end of the shaft. The method further includes the step of moving a guide wire into and through the channel, relative to the shaft. The method may further include the step of advancing the catheter over the guide wire.

In another embodiment, the present invention includes a method of exchanging a catheter during a biliary endoscopic procedure. The method includes the step of passing an endoscope, having a lumen extending longitudinally therethrough, through a patient's mouth into the alimentary canal. A distal end of the endoscope is positioned proximate an opening into the biliary tree. A guide wire is passed through the lumen of the endoscope.

A catheter is provided having a guide wire lumen carried by the shaft, extending from a location proximal of a distal end of the shaft to a location proximate the distal end of the shaft. The shaft includes a channel into the guide wire lumen, located distal of the proximal end of the shaft. The channel is defined by a channel proximal end and a channel distal end. The catheter is advanced over the guide wire, wherein a proximal end of the guide wire exits from the channel. The method further comprises the step of passing the guide wire radially through the channel opening while inserting or retracting the catheter until the guide wire exits the second opening.

BRIEF DESCRIPTION OF THE DRAWINGS

The invention will be further described with reference to the accompanying drawings, wherein like numbers refer to like parts in several views and wherein:

FIG. 1 is a perspective view of a catheter in accordance with the present invention having a U-shaped channel and guide wire lumen for directing a guide wire along its shaft and for facilitating rapid catheter exchange;

FIG. 1C is an enlarged fragmentary perspective view of the encircled catheter section of FIG. 1 at 1C;

FIG. 3 is a perspective view of an endoscope exchange sheath assembly, without slit, suitable for receiving the catheter of FIG. 1;

FIG. 3A is an enlarged fragmentary perspective view of the encircled sheath section of FIG. 3 at 3A;

FIG. 4 is a perspective view of an alternative embodiment sheath assembly having a slit sheath and two-piece hub, shown in unlocked position;

FIG. 4A is a perspective view of the two-piece hub of FIG. 4 in locked position;

FIG. 4B is an enlarged fragmentary perspective view of the encircled sheath section of FIG. 4 at 4B, having a slit;

FIG. 4C is an enlarged fragmentary perspective view of a sheath section, having an overlap, an alternate embodiment of the sheath in FIG. 4B;

FIG. 7 is a partial perspective view of a guide wire within the catheter of FIG. 1 inserted through the endoscope sheath assembly of FIG. 4, which is in turn within an endoscope;

FIG. 7A is a perspective view of the sheath assembly of FIG. 7, having the catheter removed;

FIG. 8 is a partial perspective view of an alternative embodiment of a sheath assembly, including an introducer;

FIG. 8A is an enlarged perspective view of the introducer of FIG. 8;

FIG. 9A is an enlarged, cross-sectional view of an alternative embodiment of the introducer of FIG. 8;

FIG. 9B is an enlarged, cross-sectional view of another alternative embodiment of the introducer of FIG. 8;

FIG. 9C is an enlarged, cross-sectional view of another alternative embodiment of the introducer of FIG. 8;

FIG. 9D is an enlarged, cross-sectional view of another alternative embodiment of the introducer of FIG. 8;

FIG. 9E is an enlarged, perspective view of another alternative embodiment of the introducer of FIG. 8;

FIG. 9F is an enlarged, cross-sectional view of another alternative embodiment of the introducer of FIG. 8;

FIG. 10 is a partial elevational view of a catheter showing another application of the present invention; and FIG. 11 is a partial elevational view of a catheter showing another application of the present invention.

DETAILED DESCRIPTION OF THE INVENTION

Figure 1B:
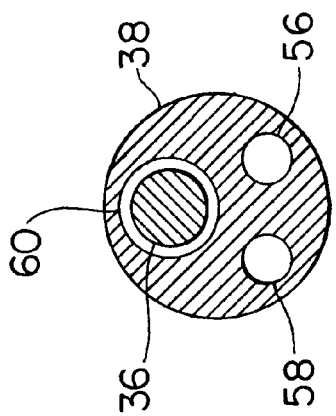
FIG. 1B is a cross-sectional view of the catheter with guide wire of FIG. 1 taken along the line 1B—1B.

FIG. 1 shows a perspective view of a catheter assembly 30 in accordance with the present invention. Catheter assembly 30 is used in catheter procedures for accessing targeted anatomical regions through the alimentary canal. The present invention incorporates features which allow rapid exchange of catheter by a single operator. The catheter of the present invention allows shorter length guide wires to be used, resulting in procedures which require less medical personnel, are less time consuming, and less costly. Additionally, the present invention is adaptable to most catheter devices used for catheter procedures within the alimentary canal.

Catheter assembly 30 includes a catheter hub assembly 32 and a catheter 34, having a guide wire 36 passing through a portion thereof. Catheter 34 includes a shaft 38, which in general terms has a proximal end 40, a U-channel 42, a distal tip region 44, a distal end 46 and various lumens described in greater detail below. Catheter hub assembly 32 is operably connected to proximal end 40 of shaft 38. Catheter hub assembly 32 is preferably configured to couple to ancillary devices allowing access to a lumen within shaft 38.

Shaft 38 is a generally tubular shaped member having a generally uniform outer shape at proximal end 40. Shaft 38 may be sized for slidable passage through the lumen of an endoscope (not shown). Shaft 38 is preferably formed in an extrusion process. Shaft 38 may be formed of an extruded polymeric material. In one embodiment, the preferred polymeric material is polytetrafluoroethylene, polyether block amide, nylon or a combination or blend of these. Catheters which are contemplated include, but are not limited to, cannulas, sphincterotomes, cytology devices, and devices for stone retrieval and stent placement.

In a preferred embodiment, shaft 38 further includes a distal taper 48 which tapers to distal tip region 44. Additionally, tip region 44 may include high contrast, color coded distal markers 50. Finally, distal end 46 may be radiopaque for fluoroscopic visualization of distal tip region 44 during a catheter procedure. It should be understood, however, that these additional features are in no way required elements.

U-channel 42 of shaft 38 extends between a first, proximal channel end 52 and a second, distal channel end 54. U-channel 42 serves to contain, but not necessarily constrain, guide wire 36, between channel proximal end 52 and channel distal end 54. The term "U-channel" refers to a channel shape that allows radial removal of guide wire 36 from the channel 42, and need not be strictly in the shape of the letter U. Channel 42 in the preferred embodiment is sufficiently large to allow unhindered radial guide wire 36 movement out of channel 42. Further, the channel walls and radial opening are substantially equal to or slightly larger than the diameter of a guide wire lumen, described in greater detail below. Although it is recognized that proximal channel end 52 may be located at any location distal of proximal end 40 of shaft 38, channel distal end 54 is preferably located between 10 and 40 cm from distal end 46 of catheter shaft 38.

Figure 1A:
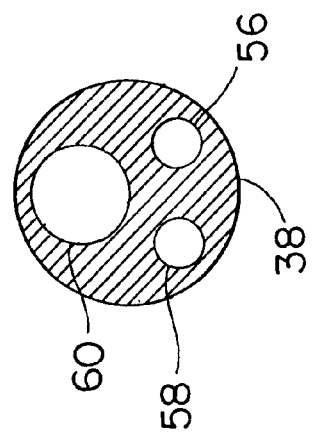
FIG. 1A is a cross-sectional view of the catheter of FIG. 1 taken along the line 1A—1A.

Finally, as shown in FIG. 1A, which is a cross-sectional view of shaft 38 taken along line 1A—1A at a location proximal of channel proximal end 52, shaft 38 includes ancillary lumen 56, ancillary lumen 58 and guide wire lumen 60.

Ancillary lumen 56 and ancillary lumen 58 extend longitudinally between proximal end 40 and distal end 46 of shaft 38. Ancillary lumen 56 and ancillary lumen 58 may be injection lumens, allowing for high contrast media flow capability for bubble-free opacification and for excellent visualization of a desired anatomical region. Additionally or alternatively, ancillary lumen 56 and/or ancillary lumen 58 may be used for or as part of other ancillary devices, such as a cutting wire lumen or a retrieval balloon lumen.

Guide wire lumen 60 extends longitudinally between proximal end 40 and distal end 46 of shaft 38 in the preferred embodiment. Further, guide wire lumen 60 is sized to receive guide wire 36. Guide wire lumen 60 may be a tubular member which is extruded integral catheter shaft 38, or alternatively, guide wire lumen 60 may be a separate tubular member which is coupled to catheter shaft 38. Although in one preferred embodiment the guide wire lumen 60 is a tubular member which is located proximate distal end 46 of catheter shaft 38, it is recognized that guide wire lumen 60 may be formed anywhere along shaft 38, may be an extension of shaft 38 coupled to distal end 46, or guide wire lumen 60 may run the entire length of shaft 38.

Referring to FIG. 1B, a cross-sectional view of shaft 38 taken along line 1B—1B of FIG. 1 is shown. Guide wire 36 may access guide wire lumen 60 at a point proximal channel distal end 54. Guide wire 36 extends within channel 42 to channel distal end 54, continuing within guide wire lumen 60 through distal tip region 44, and exiting through an opening in distal end 46.

Referring to FIG. 1C, a section of catheter shaft 38 having U-channel 42 is shown. The embodiment shown also includes ancillary lumens 56 and 58. Sections of shaft 38 proximate the channel proximal end 52 and distal channel distal end 54 contain guide wire lumen 60 in communication with U-channel 42. In one embodiment, U-channel 42 has an interior, closed-side geometry, substantially the same as the geometry of guide wire lumen 60. Further, U-channel 42 walls are spaced further than a diameter of guide wire 36 such that guide wire 36 moves freely into and out of U-channel 42.

Catheter shaft 38 can be configured such that U-channel 42 is defined separately from guide wire lumen 60. With this approach, guide wire lumen 60 is divided into two sections; a first section extending between proximal end 40 of shaft 38 and channel proximal end 52; and a second portion extending between channel distal end 54 and distal end 46 of shaft 38. Alternatively, the shaft can be configured to define guide wire lumen 60 as extending longitudinally between proximal end 40 and distal end 46 of shaft 38. In the alternative embodiment, between channel proximal end 52 and channel distal end 54, guide wire lumen 60 is integral with U-channel 42. In other words, guide wire lumen 60 defines a portion of U-channel 42 such that spacing between outer walls of U-channel 42 is equal to a diameter of guide wire lumen 60. Regardless of how guide wire lumen 60 and U-channel 42 are defined, U-channel 42 provides for access to guide wire lumen 60 at channel distal end 54. In this regard, channel distal end 54 can be enlarged to more easily direct guide wire 36 into guide wire lumen 60.

Guide wire lumen 60 and U-channel 42 allow rapid exchange of catheter assembly 30 when an alternative catheter is necessary during a certain medical procedure. Shorter length guide wires may be used since guide wire 36 does not pass through shaft proximal end 40 and hub assembly 32, but rather exits the catheter shaft 38 at U-channel 42 located substantially distal from proximal end 40. The unique catheter construction in accordance with the present invention will reduce catheter therapeutic and diagnostic procedure time since catheter device exchanges may be performed relatively more easily and quickly by a single operator. Additional personnel and time associated with maintaining the placement of a conventional (approximately 400 cm) guide wire within the targeted anatomical region is eliminated, reducing the overall costs of the procedure.

Figure 2A:
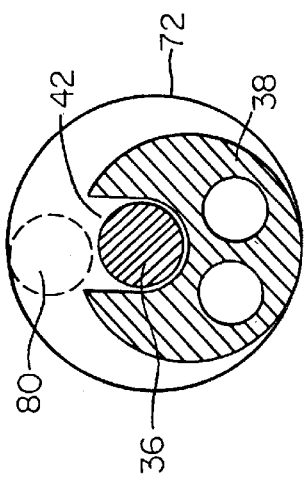
FIGS. 2A–2D are cross-sectional views of the catheter of FIG. 1 located within increasingly larger endoscope channels.

Referring to FIGS. 2A through 2D, cross-sectional views of endoscope working channels 70–76 containing a catheter according to FIG. 1 are shown. In the examples illustrated in FIGS. 2A through 2D, working channel inside diameters 70, 72, 74, and 76 are 2.8, 3.2, 3.8, and 4.2 mm, respectively. FIG. 2A illustrates catheter shaft 38 having ancillary lumens 54 and 56, U-channel 42, and guide wire 36 within U-channel 42. Further, shaft 38 is shown within a first size endoscope working channel 70. In FIG. 2A, guide wire 36 is effectively radially constrained by small sized working channel 70 that closely surrounds U-channel 42.

Figure 2B:
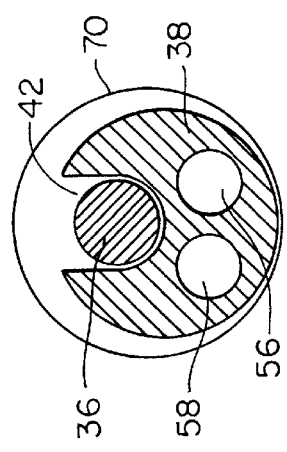
Figure 2C:
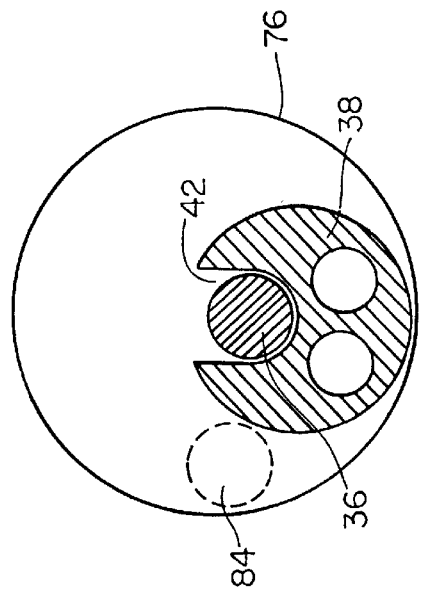

FIG. 2B illustrates catheter containment within a second size working channel 72, slightly larger than the working channel 70 of FIG. 2A. In FIG. 2B, guide wire 36 is able to move out of U-channel 42 to a position denoted with dashed lines at 80. FIG. 2C shows shaft 38 contained within a third, even larger sized working channel 74. Guide wire 36 is able to move completely out of U-channel 42 to position 82 shown with dashed lines. Finally, FIG. 2D demonstrates catheter shaft 38 within a fourth size working channel 76. In this even larger working channel, guide wire 36 lies within an even larger cross-sectional area, and is able to move to a position shown in FIG. 2D with dashed lines at 84.

As shown with the larger endoscope working channels (FIGS. 2C and 2D), the potential for guide wire 36 to slip out of U-channel 42 creates a potential for the guide wire 36 to become pinched and restrict desired movements of both guide wire 36 and catheter shaft 38. For this reason, when larger endoscope working channels are used, an exchange sheath having a sufficiently small inner diameter so as to constrain guide wire movement to within the catheter U-channel 42 is employed with the preferred embodiment. Generally speaking, an endoscope exchange sheath in accordance with the preferred embodiment allows for use of a radially accessible guide wire, which is longitudinally aligned with the catheter, while presenting a circular profile to an endoscope and mitigating guide wire pinching problems between the catheter and the endoscope working channel wall.

Referring to FIG. 3, an endoscope exchange sheath assembly 100 having sheath hub assembly 102 and a sheath 104 is shown. The sheath 104 includes a lumen 106 and a distal end 108. FIG. 3A shows a section of sheath 104, having lumen 106 for receiving a catheter. Basically, with reference to FIG. 1, catheter 34 is fed through lumen 106 of sheath 104 such that sheath 104 encompasses guide wire 36 within U-channel 42. Sheath 104 is adapted to be disposed within an endoscope working channel, thereby providing a smaller diameter channel than that of the surrounding endoscope working channel constraining the guide wire 34 (FIG. 1) to the U-channel 50 (FIG. 1), and mitigating the potential problems shown in FIGS. 2C and 2D.

Referring to FIG. 4, an alternate endoscope exchange sheath assembly 110 is shown. Sheath assembly 110 includes a two-piece hub assembly 112 and a sheath 114 defining lumen 116 and having slit 118 extending longitudinally over its length, terminating at distal end 120. Slit 118 in sheath 114 is shown in more detail in FIG. 4B.

Referring again to FIG. 4, two-piece hub assembly 112 has a proximal hub portion 122 and a distal hub portion 124, having a proximal slit 126 and a distal slit 128, respectively. Sheath slit 118 is in communication with hub slits 126 and 128, allowing a guide wire (not shown) to be radially slid into or out of sheath assembly 110. Proximal hub portion 122 is shown unlocked (position "A") in FIG. 4, aligning hub proximal slit 126 with hub distal slit 128 and sheath slit 118, providing a continuous slit for guide wire radial movement into and out of the sheath assembly 110. Proximal hub portion 122 is shown locked, in position "B", in FIG. 4A, whereby proximal hub slit 126 is rotated with respect to distal hub slit 128, preventing a guide wire (not shown) within hub assembly 112 from being moved radially out of hub assembly 112. Proximal hub portion 122 is set to position B (FIG. 4A) when radial guide wire movement is not desired.

FIG. 4C illustrates a portion of an alternate embodiment sheath 130 having a lumen 132, a sheath wall opening 134 and sheath wall overlap 136. A guide wire (not shown) is able to be slid out of lumen 132 of sheath 130 by maneuvering the guide wire into sheath wall opening 134 and through overlap 136.

Figure 5:
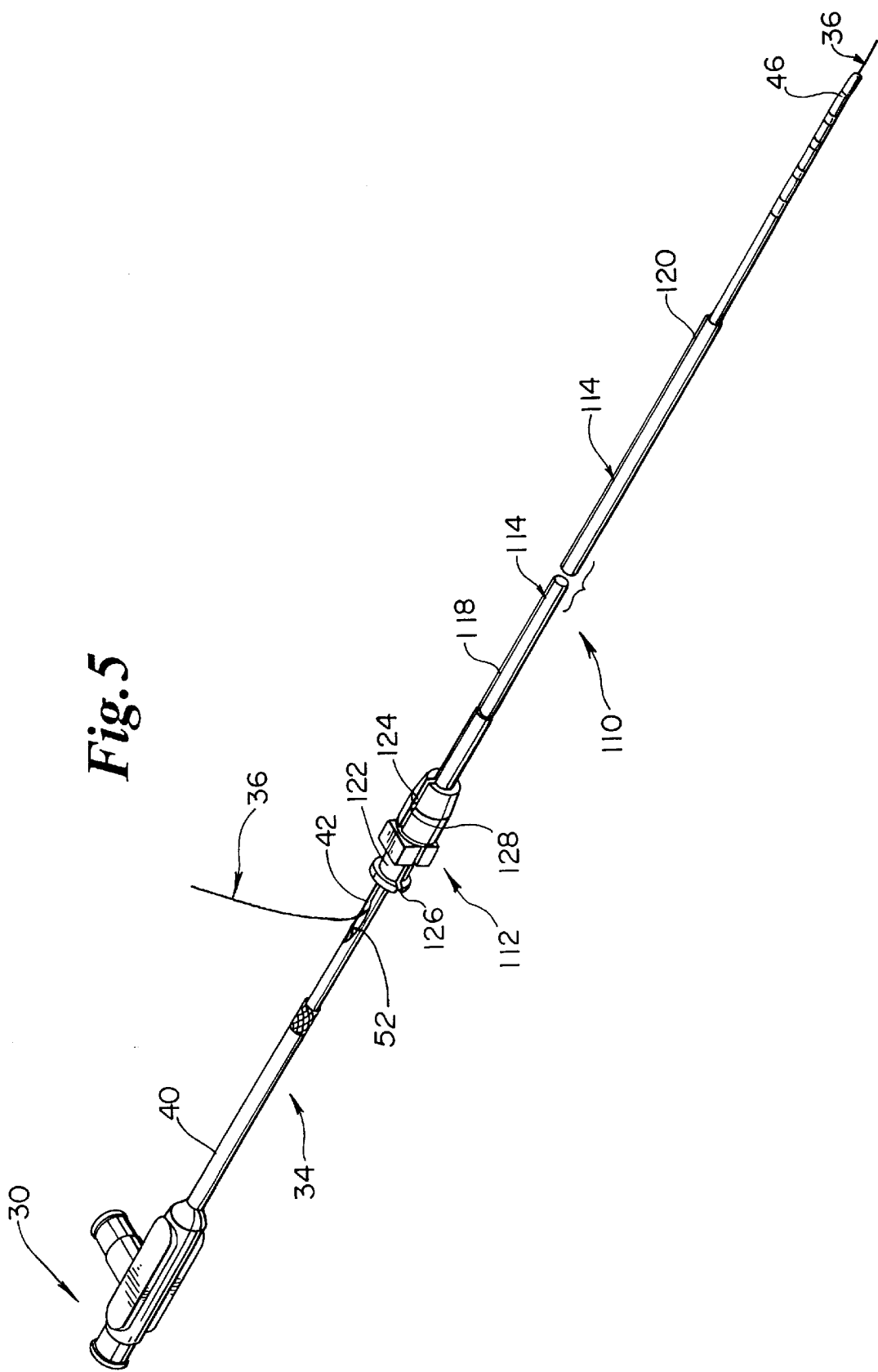
FIG. 5 is a perspective view of the catheter of FIG. 1 inserted through the endoscope sheath assembly of FIG. 4.

Referring to FIG. 5, catheter assembly 30 depicted in FIG. 1 is shown inserted within endoscope exchange sheath assembly 110 depicted in FIG. 4. More particularly, catheter 34 is inserted through slitted sheath assembly 110, extending distally out sheath distal end 120. Guide wire 36 (shown partially in FIG. 5) is positioned within U-channel 42 of catheter 34, along guide wire lumen 60 (FIG. 1B), and extends from shaft distal end 46. Further, guide wire 36 is engaged by hub assembly 112. More particularly, guide wire 36 passes within and is engaged by proximal slit 126 and distal slit 128 of hub assembly 112. Sheath proximal hub portion 122, having proximal slit 126, is shown in locked position relative to sheath distal hub portion 124, having distal slit 128. Thus, in the locked position, hub assembly 112 of sheath assembly 110 prevents radial withdrawal of guide wire 36, otherwise inserted in U-channel 42 of catheter 34, from distal the channel proximal end 52.

Figure 2D:
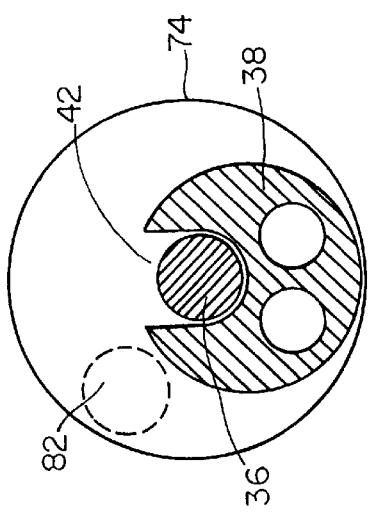
Figure 6:
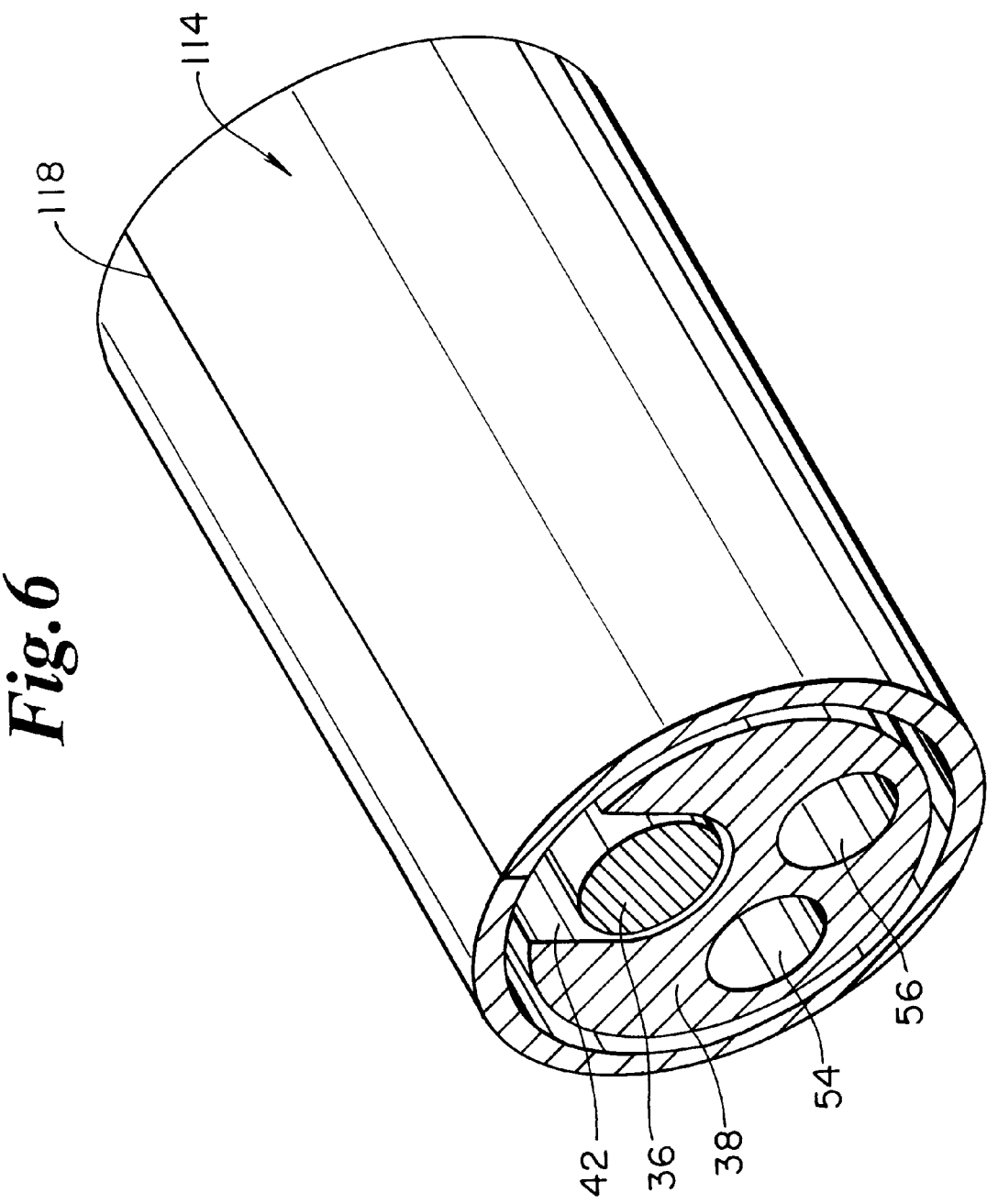
FIG. 6 is a perspective view of a endoscope sheath section containing a catheter having a U-shaped channel containing a guide wire.

Referring to FIG. 6, a section of FIG. 5 is shown in detail, having endoscope sheath 114 containing catheter shaft 38, which further maintains guide wire 36 within U-channel 42. As shown, sheath 114 is able to constrain movement of guide wire 36 from U-channel 42 when sheath 114 is within a larger endoscope working channel, for example as illustrated in FIGS. 2C and 2D. Importantly, the sheath 114 embodiment illustrated in FIG. 6 includes longitudinal slit 118, allowing guide wire 36 to be peeled from catheter shaft 38 and endoscope sheath 114. In other words, as previously described, U-channel 42 is sized larger than guide wire 36 such that guide wire 36 can displace radially from U-channel 42. Sheath 114 prevents undesired displacement of guide wire 36 from U-channel 42 under normal operating conditions. However, if adequate radial force is placed on guide wire 36 by an operator, guide wire 36 will separate sheath 114 along slit 118 such that guide wire 36 is displaced from sheath 114 and U-channel 42.

Referring to FIG. 7, guide wire 36 is shown inserted within catheter assembly 30 of FIG. 1, which is inserted through endoscope sheath assembly 110 of FIG. 4, which is in turn within an endoscope 150. Sheath assembly 110 includes sheath 114 that has slit 118 and two-piece hub assembly 112, shown at a locked position "B" (also in FIG. 4A). Having hub assembly 112 locked prevents guide wire 36 from moving radially out of sheath 114 through slit 118. Guide wire 36 can be restrained from longitudinal movement by applying finger pressure on the guide wire 36 against hub assembly 112.

Referring to FIG. 7A, endoscope 150 and sheath assembly 110 of FIG. 7 are shown without the catheter assembly 30 inserted, as after catheter withdrawal. Sheath hub assembly 112 is shown in unlocked position at "A" (also in FIG. 4). Having hub assembly 112 unlocked allows radial movement of guide wire 36 out of sheath 114 through slit 118, but such movement may be restrained by trapping guide wire 36 against the outside of sheath 114 using one finger, providing ease of guide wire 36 control during catheter exchanges.

In one possible endoscopic procedure, an endoscope 150, as illustrated in FIG. 7, is first introduced into the mouth of a patient and is guided through the patient's alimentary canal. Specifically, endoscope 150 is guided down the esophagus, through the stomach, past the pyloric sphincter of the stomach and into the duodenum. Endoscope 150 has a lumen extending longitudinally between its proximal end and the distal end.

Endoscope 150 is guided through the alimentary canal until a distal end (not shown) of endoscope 150 is proximate the target area within the anatomy to receive treatment. In an endoscopic biliary procedure, endoscope 150 is guided into the duodenum until the opening at the distal end of the endoscope 150 is proximate the papilla of vater. The papilla of vater is located between the sphincter of oddi, which leads to the common bile duct, hepatic, and pancreatic ducts. The proximal end (shown in FIGS. 7 and 7A) of endoscope 150 extends and remains outside the mouth of the patient.

With endoscope 150 properly positioned within the patient, catheter assembly 30 is prepared for insertion into the endoscope. First, guide wire 36 is fed into the guide wire lumen 60 (FIGS. 1A–1C) of shaft 38. More particularly, a distal end of guide wire 36 is placed within U-channel 42, distal the channel proximal end 52. The guide wire 36 is then fed to channel distal end 54 (FIG. 1) into guide wire lumen 60. Finally, guide wire 36 is fed through shaft 38 to distal tip region 40 (FIG. 1). In one method, catheter 32 is then inserted directly into endoscope 150 working channel. This method may be practiced with an endoscope having a sufficiently small working channel inside diameter, as illustrated in FIG. 2A, to constrain guide wire 36 movement without a sheath.

However, in a preferred method (with reference to FIG. 7), catheter assembly 30, threaded with guide wire 36, is inserted into sheath assembly 110, thereby constraining guide wire 36 from slipping radially out of U-channel 42. More particularly, catheter 34 is inserted into endoscope 150 working channel, but leaving channel proximal end 52 proximate sheath hub assembly 112, and leaving a portion of guide wire 36 extending from the channel proximal end 52 as well. Notably, sheath hub assembly 112 includes hub slits 126 and 128 which receive a portion of guide wire 36. Thus, in the preferred embodiment, hub assembly 112 is locked, preventing unwanted radial guide wire 36 movement. In a preferred method, the loading of guide wire 34 into catheter shaft 38 and catheter shaft 38 into sheath assembly 110 is done prior to inserting endoscope 150 into a patient (not shown).

Endoscope sheath 114, containing catheter shaft 38, is inserted into endoscope 150 working channel. Endoscope sheath 114 serves to constrain radial guide wire 36 movement over the approximate length of U-channel 42. Catheter shaft 38 and sheath 114 are inserted together into endoscope 150 until both are near a distal end (not shown) of endoscope 150. Catheter shaft 38 and sheath 114 may be, either or both, advanced until exiting the distal end of endoscope 150.

In one method, guide wire 36 is advanced until guide wire 36 distal tip is positioned within the target area in the biliary tree (including the common bile, hepatic or pancreatic ducts). For example, the distal tip of guide wire 36 may be guided through the orifice leading to the papilla of vater for access to the biliary tree. Catheter shaft 38 may then be advanced over guide wire 36, tracking catheter assembly 30, until catheter distal tip region 40 (FIG. 1) exits distal end of endoscope 150 and is positioned within the desired duct. In another method, guide wire 36 and catheter assembly 30 are advanced together until catheter distal end 42 (FIG. 1) is positioned at the target area. It is also recognized that the catheter could be first advanced to near the target area, followed by inserting the guide wire when needed to advance the catheter further.

Once guide wire 36 is in position at the target area, catheter procedures, including injecting contrast media, such as radiopaque dye, through ancillary lumens 56 or 58 (FIGS. 1A–1C) into the common bile duct for visualization of the duct, can be performed. After the desired catheter procedure has been completed, catheter assembly 30 can be exchanged or removed from endoscope 150, leaving guide wire 36 in position for other catheter procedures. Catheter assembly 30 and sheath assembly 110 may also be removed together.

One method of withdrawing catheter 34 from endoscope 150 is possible using either a slitted/overlapped endoscope sheath 114 as depicted in FIGS. 4 through 5C, or a sheath 104 without a slit as depicted in FIGS. 3 through 3A. Using this method, best visualized with reference to FIG. 7, guide wire 36 is held to prevent longitudinal movement while catheter 34 is retracted within endoscope sheath 114 (or 104). Catheter 34 retraction leaving the guide wire 36 in position within the patient is enabled by U-channel 42 being radially open to guide wire 36 removal in catheter shaft 36. Once catheter retraction has brought channel distal end 54 (FIG. 1) to a point proximate sheath hub assembly 112, only a relatively short portion of guide wire 36, from channel distal end 54 to distal end 46 (FIG. 1) of catheter shaft 38, remains within catheter 34. A single operator can remove this remaining portion of guide wire 36 from catheter 34 by first slightly retracting catheter assembly 30 (while still holding guide wire 34 in place) out of sheath assembly 110 (or 100), such that a portion of guide wire 36 is accessible distal of catheter distal end 46. In other words, a small portion of guide wire 36 is accessible between distal end 46 of catheter 34 and distal hub portion 124 of sheath assembly 110. The accessible portion of guide wire 36 is then held by the operator, while withdrawing the remaining portion of catheter 34 completely over guide wire 36. In an alternative method, the distal end of the endoscope can include an elevator which could be utilized to lock the distal end of the guide wire in position while the catheter is removed.

Exchange of endoscope sheath assembly 110 may be desired, as when a stent (not shown) is to be advanced over guide wire 36, and the stent has a larger outside diameter than can be accommodated by the sheath 114. One method of exchanging an endoscope sheath assembly 110 may be used where sheath 114 is slitted as in FIG. 4B, or overlapped, as in sheath 130 in FIG. 4C. Referring to FIG. 7A, two-piece hub assembly 112 is turned to the unlocked position "A" (also shown in FIG. 4). Guide wire 36 is pulled radially away from sheath hub assembly 112 and through slit 118 in sheath 114. Guide wire 36 is then held, preferably against some portion of endoscope 150, to prevent guide wire 36 from being dislodged from position within the patient. Sheath 114 is retracted from endoscope 150, guide wire 36 being "peeled" away from sheath 114. Sheath retraction is continued until sheath 114 is completely outside of endoscope 150 and over guide wire 36. At this point, guide wire 36 is within endoscope 150 working channel, and stents, catheters, and endoscope sheaths may be advanced over guide wire 36.

Another method of exchanging both endoscope sheath assembly 110 and catheter assembly 30 may be used where the sheath 114 is slitted as in FIG. 4B, or overlapped, as in sheath 130 in FIG. 4C. Referring to FIGS. 7 and 7A, two-piece hub assembly 112 is turned to the unlocked position "A" (FIG. 7A). Guide wire 36 is pulled radially away from U-channel 42 of catheter 34, from hub assembly 112 and through slit 118 in sheath 114. Guide wire 36 is then held, preferably against some portion of endoscope 150, to prevent guide wire 36 from being dislodged from position within the patient. Sheath 114 and catheter 34 are retracted from endoscope 150, with guide wire 36 being "peeled" away from sheath 114. Sheath assembly 110 and catheter assembly 30 retraction are continued until sheath 114 and catheter 34 are completely outside of endoscope 150 and over guide wire 36. At this point, guide wire 36 remains in a position within endoscope 150 and patient. A single operator can access a small portion of guide wire 36 between distal end 46 (FIG. 1) of catheter 34 to hold guide wire 36 in place while catheter assembly 30 is completely removed or disengaged from guide wire 36.

While sheath assembly 110 has been described as including a two-piece hub assembly 112 in conjunction with sheath 114, other assemblies may be used. For example, referring to FIG. 8, an alternate sheath assembly 160 is shown. Sheath assembly 160 includes an introducer 162, an attachment means 164 and a sheath 166. Similar to previous embodiments, sheath 166 defines a lumen (not shown) and includes a slit 168 extending longitudinally over its length, terminating at a distal end 170. Sheath 166 is generally identical to sheath 104 and sheath 114 previously described. Introducer 162 is attached to sheath 166 by attachment means 164 such that lumen (not shown) of sheath 166 is in fluid communication with an interior portion of introducer 162. In one preferred embodiment, attachment means 164 is a flexible membrane which seals sheath 166 to introducer 162. Alternatively, other forms of attachment, such as an adhesive or frictional engagement between introducer 162 and sheath 166 may also be useful.

Referring to FIG. 8A, introducer 162 is shown in greater detail. Introducer 162 is a funnel-shaped device including a horn 172 and a neck 174. In one preferred embodiment, horn 172 and neck 174 are integrally formed as a singular body.

Horn 172 is preferably a conically-shaped body having an outer wall 176. Outer wall 176 defines an interior space and includes a guide wire-receiving notch 180 formed near proximal end 182 of horn 172. Guide wire-receiving notch 180 is preferably J-shaped and includes an entry end 184 and a locking end 186. As shown in FIG. 8A, entry end 184 is open at proximal end 182 of horn 172. Conversely, locking end 186 is closed.

Neck 174 is preferably tubular in shape, and includes a passage 188. Passage 188 is configured to be in fluid communication with interior space of horn 172. In the preferred embodiment, horn 172 and neck 174 are formed of a plastic material. Alternatively, any other semi-rigid or rigid, surgically-safe material may be used.

Referring to FIGS. 1, 8 and 8A, during use, catheter assembly 34 (FIG. 1) is inserted within sheath assembly 160. More particularly, distal end 46 (FIG. 1) of catheter shaft 38 (FIG. 1), including guide wire 36 (FIG. 1) is placed within horn 172 of introducer 162. The conical shape of horn 172 assists in directing distal end 46 of catheter shaft 38, including guide wire 36, into passage 188 of neck 174. Catheter shaft 38 continues forward within lumen (not shown) of sheath 166 until distal end 46 of catheter shaft 38 extends from distal end 170 of sheath 166.

Once properly inserted within sheath assembly 160, a proximal end of guide wire 36 (FIG. 1) is maintained within guide wire-receiving notch 180. More particularly, a portion of guide wire 36 is forced by an operator through entry end 184 of guide wire-receiving notch 180 and forced within locking end 186 thereof. In this regard, locking end 186 preferably has a diameter slightly smaller than that of guide wire 36. Thus, locking end 186 frictionally maintains guide wire 36. Conversely, guide wire 36 can easily be released from guide wire-receiving notch 180 by sliding guide wire 36 from locking end 186 and out of entry end 184. Thus, sheath assembly 160 functions in a manner highly similar to sheath assembly 100 and sheath assembly 110 previously described.

Referring to FIG. 9A, an alternative embodiment of an introducer 190 is shown. Introducer 190 includes a horn 192, a neck 194 and a valve 196. Similar to previous embodiment, horn 192 and neck 194 are preferably integrally formed as a singular body. Horn 192 includes an outer wall 197 which defines a guide wire-receiving notch 198 and valve-receiving slots 200. Valve 196 includes a valve body 202 sized to fit within outer wall 197 of horn 192. Further, valve 196 includes ribs 204 extending from valve body 202. Ribs 204 are preferably sized to mate within valve-receiving slots 200 of horn 192. Thus, valve 196 is maintained within horn 192 via interaction of ribs 204 with valve-receiving slots 200. In this regard, valve-receiving slots 200 are preferably positioned along horn 192 proximal neck 194. Valve 196 is preferably made of a rubber-type material.

During use, introducer 190 functions in a manner highly similar to introducer 162 (FIGS. 8 and 8A) previously described. Additionally, however, valve 196 forms a seal about catheter shaft 38 (FIG. 1). Thus, upon insertion into a human body, valve 196 prevents bodily fluids, such as bile, from backing up through the sheath assembly. Additionally, valve 196 can provide for aspiration, if desired.

Referring to FIG. 9B, an alternative embodiment of an introducer 206 is shown. Introducer 206 is highly similar to introducer 190 (FIG. 9A) previously described. In this regard, introducer 206 includes a horn 208, a neck 210 and a valve 212. Horn 208 is preferably integrally formed with neck 210 and includes an outer wall 214 defining a guide wire-receiving notch 216 and valve-receiving slots 218. Similar to valve 196 (FIG. 9A), valve 212 includes a valve body 220 and ribs 222. Ribs 222 are sized to mate within valve-receiving slots 218 of horn 208. In this regard, valve-receiving slots 218 are positioned proximate a proximal end 224 of horn 208. Introducer 206, including valve 212, functions in a manner highly similar to introducer 190 (FIG. 9A) as previously described.

It is recognized that the fluid blocking function provided by valve 212 can be achieved with other designs. For example, referring to FIG. 9C, an alternative embodiment of an introducer 226 is shown. Introducer 226 includes a horn 228, a neck 230 and an O-ring 232. Horn 228 and neck 230 are preferably formed as an integral body. Horn 228 preferably includes a guide wire-receiving notch (not shown) similar to that previously described and an interior slot 234. Interior slot 234 is preferably positioned proximate neck 230 and is sized to maintain O-ring 232. Alternatively, interior slot 234 can be formed in neck 230.

O-ring 232 is preferably made of a rubber-type material. Further, O-ring 232 has an inner diameter slightly smaller than that of horn 228 and neck 230. Thus, during use, O-ring 232 forms a seal about catheter shaft 38 (FIG. 1), blocking passage of bodily fluids, such as bile, into horn 228.

Referring to FIG. 9D, another alternative embodiment of an introducer 236 is shown. Introducer 236 is similar to a touhey-borst system and includes an upper horn section 238, a lower horn section 240 and a grommet 242. Upper horn section 238 includes an outer wall 244 defining a proximal end 246, a grommet-receiving flange 248 and a distal end 250. Proximal end 246 of horn section 238 preferably includes a guide wire-receiving notch (not shown) similar to that previously described. Distal end 250 is threaded and includes a passage 252 sized to receive a portion of lower horn section 240.

Lower horn section 240 includes a body 254 defining a proximal end 256, an intermediate portion 258 and a distal end 260. An interior passage 266 is configured to communicate with passage 252 and extends from proximal end 256 to distal end 260. Finally, proximal end 256 includes a threaded slot 262 sized to threadably receive distal end 250 of upper horn section 238.

Grommet 242 is preferably made of a rubber-type material and is sized to nest within grommet-receiving flange 248 of upper horn section 238 while abutting proximal end 256 of lower horn section 240.

Introducer 236 is assembled by placing grommet 242 within grommet-receiving flange 248 of upper horn section 238. Distal end 250 of upper horn section 238 is then threadably secured to proximal end 258 of lower horn section 240. As upper horn section 238 is threadably secured to lower horn section 240, proximal end 256 of lower horn section 240 compresses grommet 242 within grommet-receiving flange 248 of upper horn section 238.

During use, introducer 236 functions in a manner highly similar to that previously described. In this regard, grommet 242 forms a seal about catheter shaft 38 (FIG. 1). Further, aspiration can be achieved, if desired, by loosening lower horn section 240 relative to upper horn section 238.

Referring to FIG. 9E, yet another alternative embodiment of an introducer 266 is shown. Introducer 266 includes a horn 268, a neck 270 and a valve 272. Preferably, horn 268, neck 270 and valve 272 are integrally formed as a singular body. In this regard, valve 272 is formed while molding horn 268 and neck 270 by imparting a controlled flash at distal end 274 of neck 270.

Introducer 266 performs in a manner highly similar to that previously described. Thus, valve 272 forms a seal about catheter shaft 38 (FIG. 1), thereby preventing back flow of bodily fluids, such as bile, into horn 268.

Referring to FIG. 9F, another alternative embodiment of an introducer 276 is shown. Introducer 276 includes a horn 278, a neck 280 and a valve 282. Horn 278 and neck 280 are preferably integrally formed as a singular body. In this regard, horn 278 and neck 280 are defined by an outer wall 284. Outer wall 284 forms a guide wire-receiving notch 286 and an exterior slot 288. Guide wire-receiving notch 286 is similar to that previously described. Exterior slot 288 is positioned along neck 280 and is sized to maintain a portion of valve 282. Alternatively, exterior slot 288 can be positioned along horn 278.

Valve 282 is preferably a rubber-type sock defined by an upper rib 290, a sidewall 292 and a shoulder 294. Upper rib 290 is preferably sized to mount within exterior slot 288 of neck 280. Sidewall 292 is preferably flexible so as to stretch along neck 280. Finally, shoulder 294 is preferably configured to abut a distal end 298 of neck 280. With this configuration, valve 282 is placed over distal end 298 of neck 280 such that shoulder 294 contacts distal end 298. Due to the preferred flexible characteristic of valve 282, side wall 292 is stretched until upper rib 290 nests within exterior slot 288 of neck 280.

During use, the catheter shaft 38 (FIG. 1) is placed through introducer 276 such that shoulder 294 of valve 282 forms a seal about catheter shaft 38. Thus, valve 282 prevents undesired back flow of bodily fluids, such as bile.

It is recognized that the rapid exchange technology of the present invention may be utilized in different types of catheter assemblies used within the alimentary canal. Referring to FIG. 10, catheter assembly 30 is used as a rapid exchange retrieval balloon system used for stone retrieval or isolated visualization techniques. Ancillary lumens 56 and 58 (FIGS. 1A–1C) form a portion of retrieval balloon catheter 300 having a balloon 302 located at its distal end, and for passage of dye injection apparatus 304. With this embodiment, the guide wire lumen 60 (FIGS. 1A–1C) may be accessed using conventional guide wire techniques through the proximal end 48 of catheter 34 or using rapid exchange techniques, via U-channel 42.

Referring to FIG. 11, the rapid exchange catheter assembly 30 design of the present invention may be used for other alimentary canal catheter applications, such as a rapid exchange sphincterotome used for endoscopic retrograde sphincterotomy, shown using a cutting wire apparatus 310. Again, the guide wire lumen 60 may be accessed by conventional guide wire techniques at the proximal end 48 of catheter 34, or alternatively, using the rapid exchange technology of the present invention, including U-channel 42.

The rapid exchange catheter of the present invention is preferably a multi-lumen catheter. With this invention, the guide wire lumen is isolated from the ancillary lumens allowing for exceptional contrast flow for high quality opacification without the need for guide wire removal. Treatment and therapeutic devices, such as retrieval balloon catheters or catheters having cutting apparatus may be included, without interference of a guide wire located within the guide wire lumen. Additionally, isolation of the guide wire lumen from the contrast lumen minimizes the risk of bubble formation during contrast flow and produces a contrast-free guide wire surface for efficient device exchanges.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims. For example, while the rapid exchange catheter of the present invention has been preferably described as being a biliary catheter, other applications are also envisioned. Thus, the catheter of the present invention can be used with biopsy, metal stent placement, plastic stent placement, snares, baskets, etc. Additionally, the catheter of the present invention may have vascular applications, where a guide catheter is substituted for the endoscope to constrain the guide wire.

What is claimed is:

1. In a catheter for use in biliary procedures including a shaft having a proximal end and a distal end, the improvement comprising:

a guide wire lumen carried by the shaft extending from a location proximal the distal end of the shaft to a location proximate the distal end of the shaft;

a channel for accessing the guide wire lumen from a location exterior to the catheter shaft, wherein the channel extends longitudinally along the shaft between a first end and a second end, the first end being located proximal the distal end of the shaft and the second end of the channel being located proximal of the first end of the channel, said channel extending over a substantial portion of the length of said catheter shaft.

2. The catheter of claim 1 wherein the guide wire lumen is formed integral with the shaft.

3. The catheter of claim 1, further including an ancillary lumen extending between the catheter proximal end and the catheter distal end.

4. The catheter of claim 1, wherein the channel for accessing the guide wire lumen includes an opening extending through the wall of the catheter shaft into the guide wire lumen.

5. The catheter of claim 4, wherein the opening extends longitudinally between the first end and the second end in communication with the guide wire lumen.

6. The catheter of claim 5, wherein the first end of the channel is in communication with the guide wire lumen.

7. The catheter of claim 1, wherein the guide wire lumen is sized to receive a guide wire having a diameter; at least a portion of the channel having a width greater than the diameter of the guide wire to allow radial guide wire movement within the channel.

8. The catheter of claim 7, wherein the channel is formed integral with the guide wire lumen, such that the channel has a width approximately equal to a diameter of the guide wire lumen.

9. The catheter of claim 1 wherein the enlarged opening is located proximate the first end of the channel.

10. The catheter of claim 1 wherein the enlarged opening is located proximate the second end of the channel.

11. The catheter of claim 10 further comprising another enlarged opening located proximate the first end of the channel.

12. A biliary rapid exchange catheter system, comprising:
a biliary catheter sized for passage within the working passageway of an endoscope, the biliary catheter including;
a shaft having a proximal end, a distal end, and an outer wall;
the shaft having a guide wire lumen extending longitudinally therethrough, between a location proximate the distal end of the shaft and a location proximal of the distal end of the shaft, the guide wire lumen adapted for receiving a guide wire;
at least part of the outer wall of the shaft defining a channel, with the channel in communication with the guide wire lumen, an outer diameter of at least a portion of the shaft and the inner diameter of at least a portion of the working passageway of the endoscope being such that the guide wire is substantially maintained in the channel when so arranged.

13. The biliary catheter system of claim 12, wherein the guide wire lumen extends between the proximal end and the distal end of the shaft.

14. The biliary catheter system of claim 12, wherein the channel includes:
a distal opening into the guide wire lumen at a location proximal of the distal end of the shaft;
a proximal opening into the guide wire lumen at a location proximal of the distal opening; and
means extending longitudinally between the proximal opening and the distal opening for allowing a guide wire to be moved between a location exterior of the guide wire lumen and the guide wire lumen.

15. The biliary catheter system of claim 14, wherein the means for allowing the guide wire to be moved between a location exterior the guide wire lumen and the guide wire lumen includes an open channel extending longitudinally between the proximal opening and the distal opening.

16. The biliary catheter system of claim 15, wherein the guide wire lumen is sized to receive a guide wire having a diameter, and further wherein at least a portion of the open channel has a width greater than the diameter of the guide wire for allowing radial guide wire movement from the open channel.

17. The biliary catheter system of claim 15, wherein the distal opening of the open channel is in communication with a portion of the guide wire lumen.

18. The biliary catheter system of claim 15, wherein the open channel is integrally formed with the guide wire lumen.

19. The biliary catheter system of claim 15, wherein the open channel divides the guide wire lumen into a first and second section such that the first section of the guide wire lumen includes the open channel and the second section extends distally of the open channel.

20. The biliary catheter system of claim 15, wherein the open channel has a U-shape over a majority of the length between the proximal and distal openings.

21. The biliary catheter system of claim 12, wherein the guide wire lumen is defined by a tubular member, and the tubular member is formed integral with the shaft.

22. The biliary catheter system of claim 12, wherein the guide wire lumen is defined by a tubular member, and the tubular member is coupled to the shaft.

23. A biliary catheter rapid exchange system comprising:
a biliary catheter sized for passage within an endoscope including a shaft having a proximal end and a distal end;
a tubular member having a proximal end, a distal end, and a guide wire lumen extending longitudinally therethrough, the tubular member extending between a location proximate the distal end of the shaft and a location proximal of the distal end of the shaft;
a distal opening in communication with the guide wire lumen, at a location proximal of the distal end of the shaft;
a proximal opening into the guide wire lumen at a location proximal of the distal port;
means extending longitudinally between the proximal opening and the distal opening for allowing a guide wire to be moved between a location exterior of the guide wire lumen and the guide wire lumen, wherein the means for allowing the guide wire to be moved includes an open channel extending longitudinally between the proximal opening and the distal opening; and
an endoscope sheath assembly having a proximal end and a distal end and an inner passageway that is adapted to receive the catheter, the sheath assembly including a sheath at the distal end and a hub at the proximal end, an inner dimension of the passageway of the sheath and an outer dimension of the shaft being such that the guide wire is substantially maintained in the channel when so arranged.

24. The device of claim 23, wherein the inner passageway of the sheath is defined by a sheath wall, the sheath wall having a means for allowing radial removal of a guide wire contained therein.

25. The device of claim 24, wherein the means for allowing radial removal of a guide wire includes a longitudinal slit in the sheath wall.

26. The device of claim 24, wherein the means for allowing radial removal of a guide wire includes a circumferentially overlapping sheath wall.

27. A biliary rapid exchange catheter system, comprising:
a sheath having a passageway extending therethrough, the passageway having an inner dimension;
a biliary catheter sized for passage within the passageway of the sheath, the biliary catheter including;
a shaft having a proximal end, a distal end, and an outer wall;
the shaft having a guide wire lumen extending longitudinally therethrough between a location proximate the distal end of the shaft and a location proximal of the distal end of the shaft, the guide wire lumen adapted for receiving a guide wire;
at least part of the outer wall of the shaft defining a channel, with the channel in communication with the guide wire lumen;
an outer dimension of the shaft and the inner dimension of the passageway of the sheath being such that the guide wire is substantially maintained in the channel when so arranged.

28. The biliary rapid exchange catheter system of claim 27 further comprising an endoscope having a working passageway extending therethrough, the working passageway of the endoscope adapted to receive the sheath.

29. A method of positioning a biliary catheter within a patient's alimentary comprising:
providing an endoscope having a working passageway extending therethrough, the working passageway having an inner dimension;
providing a catheter having a shaft with a proximal end and a distal end, and a guide wire lumen extending from a location proximal the distal end of the shaft to a location proximate the distal end of the shaft, the shaft having a channel accessible through a sidewall thereof extending into the guide wire lumen, the channel located distal of the proximal end of the shaft, an outer dimension of at least a portion of the shaft and the inner dimension of at least a portion of the working passageway of the endoscope being such that the guide wire is substantially maintained in the channel when so arranged;
positioning the endoscope in the patient's alimentary;
positioning the catheter in the working passageway of the endoscope; and
positioning the guide wire in the guide wire lumen and the channel of the shaft.

30. The method of claim 29, further including advancing the catheter over the guide wire.

31. The method of claim 29, further including advancing the catheter and the guide wire together into the working passageway of the endoscope.

32. The method of claim 29, further including withdrawing the catheter from the working passageway of the endoscope over the guide wire.

33. The method of claim 32, further including removing the guide wire from the channel of the shaft as the catheter exits the working passageway of the endoscope.

34. A method of exchanging a catheter during a biliary endoscopic procedure comprising the steps of:
passing an endoscope having a lumen extending longitudinally therethrough, through a patient's mouth into the alimentary canal;
positioning a distal end of the endoscope proximate the opening into the biliary tree;
providing a catheter having a shaft and a guide wire lumen extending from a location proximal a distal end of the shaft to a location proximate the distal end of the shaft, and further including a channel into the guide wire lumen located distal of the proximal end of the shaft, an outer dimension of at least a portion of the shaft and an inner dimension of at least a portion of the lumen of the endoscope being such that a guide wire is substantially maintained in the channel when so arranged;
providing a guide wire through at least part of the channel; and
positioning the catheter and the guide wire in the lumen of the endoscope, with the guide wire positioned in the channel.

35. The method of claim 34, further including the step of retracting the catheter over the guide wire.

36. A system for performing biliary procedures comprising:
a catheter having a shaft with a proximal end and a distal end and a guide wire lumen extending from a location proximal the distal end of the shaft to a location proximate the distal end of the shaft, the guide wire lumen having a diameter;
means for accessing the guide wire lumen from a location exterior to the catheter shaft, located distal the proximal end of the shaft, wherein the means for accessing the guide wire lumen includes,
a first enlarged opening through the wall of the catheter shaft into the guide wire lumen located proximal the distal end of the shaft,
a second enlarged opening through the wall of the shaft located proximal the first opening, and
a channel extending longitudinally between the first enlarged opening and the second enlarged opening, wherein the channel has a width allowing for radial guide wire removal; and
an endoscope sheath assembly having a proximal end and a distal end and an inner passageway that is adapted to receive the catheter, the sheath assembly including a sheath at the distal end and a hub at the proximal end, an inner dimension of the passageway of the sheath and an outer dimension of the shaft being such that the guide wire is substantially maintained in the channel when so arranged.

37. The system of claim 36, wherein the sheath includes a lumen therethrough defining a sheath wall, the sheath wall having a means for allowing radial removal of a guide wire contained therein.

38. The system of claim 37, wherein the means for allowing radial removal of a guide wire includes a longitudinal slit in the sheath wall.

39. The system of claim 37, wherein the means for allowing radial removal of a guide wire includes a circumferentially overlapping sheath wall.

40. A method of positioning a biliary catheter within a patient's alimentary comprising:

providing a sheath having a passageway extending therethrough, the passageway having an inner dimension;

providing a catheter having a shaft with a proximal end and a distal end, and a guide wire lumen extending from a location proximal the distal end of the shaft to a location proximate the distal end of the shaft, the shaft having a channel through a sidewall thereof extending into the guide wire lumen, the channel located distal of the proximal end of the shaft, an outer dimension of the shaft and the inner dimension of the passageway of the sheath being such that the guide wire is substantially maintained in the channel when so arranged;

positioning the sheath in the patient's alimentary;

positioning the catheter in the passageway of the sheath, and positioning the guide wire in both the guide wire lumen and the channel of the shaft.

41. The method of claim 40 further comprising:

providing an endoscope with a working passageway extending therethrough;

positioning the endoscope in the patient's alimentary; and positioning the sheath in the working passageway of the endoscope.

* * * * *